(12) United States Patent
Bhattaru

(10) Patent No.: US 7,703,020 B2
(45) Date of Patent: Apr. 20, 2010

(54) MEDICAL DIAGNOSTIC SYSTEM INTERFACE

(75) Inventor: Nammalvar Venkata Bhattaru, Karnataka (IN)

(73) Assignee: General Electric Company, Schenectady, NY (US)

( * ) Notice: Subject to any disclaimer, the term of this patent is extended or adjusted under 35 U.S.C. 154(b) by 550 days.

(21) Appl. No.: 11/395,444

(22) Filed: Mar. 31, 2006

(65) Prior Publication Data

US 2007/0234219 A1    Oct. 4, 2007

(51) Int. Cl.
*G06F 3/00* (2006.01)
*G09G 5/00* (2006.01)

(52) U.S. Cl. .................... 715/740; 715/700; 715/733; 715/744; 715/765; 715/205; 714/46; 709/203; 709/217; 707/10; 702/183; 600/300

(58) Field of Classification Search ............ 715/700, 715/733, 735, 736, 740, 741, 744, 764, 765, 715/866, 961, 205; 714/100, 25, 46, 47, 714/48; 709/203, 204, 205, 217, 223, 224; 707/1, 9, 10, 104.1; 702/183; 600/300; 382/131
See application file for complete search history.

(56) References Cited

U.S. PATENT DOCUMENTS

| | | | |
|---|---|---|---|
| 5,432,934 A | | 7/1995 | Levin et al. |
| 5,550,968 A | * | 8/1996 | Miller et al. ............ 715/741 |
| 5,684,945 A | * | 11/1997 | Chen et al. .............. 714/20 |
| 6,308,273 B1 | | 10/2001 | Goertzel et al. |
| 6,325,540 B1 | * | 12/2001 | Lounsberry et al. ......... 378/207 |
| 6,516,324 B1 | * | 2/2003 | Jones et al. ............. 707/104.1 |
| 6,539,422 B1 | * | 3/2003 | Hunt et al. .............. 709/217 |
| 6,609,115 B1 | * | 8/2003 | Mehring et al. ............ 705/51 |
| 7,340,747 B1 | * | 3/2008 | Zeliger et al. ............ 719/328 |
| 2002/0112733 A1 | * | 8/2002 | Miyauchi et al. .......... 128/925 |
| 2002/0124054 A1 | | 9/2002 | Dorn et al. |
| 2003/0046548 A1 | * | 3/2003 | Brown et al. ............ 713/182 |
| 2003/0097054 A1 | * | 5/2003 | Sasaki et al. ............ 600/407 |
| 2003/0195644 A1 | * | 10/2003 | Borders et al. ............ 700/90 |
| 2005/0063575 A1 | * | 3/2005 | Ma et al. ............... 382/128 |
| 2005/0078082 A1 | * | 4/2005 | Muralidharan et al. ...... 345/156 |
| 2005/0202388 A1 | * | 9/2005 | Zuhl et al. ............. 434/350 |
| 2005/0209790 A1 | * | 9/2005 | Niethammer ............. 702/28 |
| 2006/0077439 A1 | * | 4/2006 | Yamamura et al. ......... 358/1.15 |
| 2007/0038739 A1 | * | 2/2007 | Tucker ................. 709/224 |
| 2007/0198145 A1 | * | 8/2007 | Norris et al. ............ 701/23 |
| 2008/0154751 A1 | * | 6/2008 | Miles .................. 705/28 |

* cited by examiner

*Primary Examiner*—X. L Bautista
(74) *Attorney, Agent, or Firm*—Fletcher Yoder

(57) ABSTRACT

A medical diagnostic system and method having an application configured to generate a user-interface screen comprising a plurality of interface items. A configuration file is stored on the system and includes identification data of the items and a guarded designation for at least one guarded item. A dynamic link library is configured to receive the identification data and the guarded designation from the configuration file, and a server operative on the system for serving the user-interface screen to a remote client. The guarded item of the user-interface screen served to the remote client may have an altered appearance to the remote client and/or may be inoperable to the remote client.

20 Claims, 5 Drawing Sheets

MEDICAL DIAGNOSTIC SYSTEM INTERFACE

BACKGROUND

The present invention relates generally to the remote interaction with a medical diagnostic system. More specifically, the present invention relates to the remote configuration, remote operation, and/or remote servicing of a medical diagnostic system while prohibiting remote implementation of certain functions of the system.

A wide variety of medical diagnostic systems, including but not limited to imaging technologies such as digital X-ray, tomosynthesis, X-ray mammography, computed tomography (CT), positron emission tomography (PET), electron beam tomography (EBT), magnetic resonance imaging (MRI), and so forth, have become commonplace at both large and small medical facilities. Though the number of medical diagnostic systems has increased, the number of personnel qualified to service these systems or to instruct new technicians in their use has not increased at the same rate. Furthermore, because medical imaging systems have become more commonplace at rural or less centralized locations, it may be costly to support a traveling technicians, instructors, nurses, or physicians, and so on.

One alternative solution is to allow engineers, physicians, nurses, technicians, and/or instructors to interact with imaging systems and facility personnel remotely. In this manner, travel time and costs associated with servicing remote, or even local, medical facilities may be reduced or eliminated. For example, a remote engineer may access the imaging system to perform diagnostic routines, to configure the settings used to acquire an image, to view problem images generated by facility personnel, and so forth. Similarly, a remote instructor may access the imaging system to demonstrate the settings appropriate for particular patient conditions or to demonstrate the effect of varying particular system settings in response to image irregularities or artifacts. Further, where safe and appropriate, a technician, nurse, or physician may participate remotely in the operation of the medical device.

This alternative may be unacceptable, however, due to problems associated with remote access to the imaging system. For example, a remote engineer or instructor may be able to see the user interface for the imaging system remotely, but will not be able to see the imaging device or scanner itself or the location of patients or facility personnel in relation to the device or scanner. As a result, a remote engineer or instructor may improperly move a component of the imaging system, such as a CT table or gantry, or initiate the emission of radiation or the generation of a magnetic field when the patient or personnel are not properly positioned. Therefore, in certain cases, it is desirable to allow remote servicing and instruction to be performed on a medical diagnostic system, (e.g., medical imaging system) while limiting the possibility of remote movement or particular operational aspects of the system. In general, what commands are permitted locally may be decided on a case-by-cases basis, depending on the particular circumstances of the needs, the application, and the safety considerations.

BRIEF DESCRIPTION

The present invention relates generally to providing a limited interface to remote service engineers, technicians, nurses, physicians, and/or instructors to allow remote action on a medical imaging system or other system. The technique provides for partially or completely masking portions of the system interface which the remote operator may not operate or does not need to see. In addition, actions taken by the remote operator in the prohibited or limited portions of the interface may be filtered upon transmission to the system, thereby preventing inadvertent or intentional execution of a limited or prohibited action. In this manner, information that the remote operator does not need for service or instructional purposes, such as private patient information, may be masked from the remote operator. Similarly, the remote operator may be prevented from taking actions reserved to a local operator who can visually oversee the procedure. For example, actions such as moving components of the imaging system, initiating radiation emissions, and/or generating powerful magnetic fields may be reserved for a local operator. However, again, it should be emphasized that the operational aspects accessible or not accessible to remote operation my change depending on the particular circumstances.

The present technique generally provides for limiting or guarding a remote display of a medical diagnostic-system user interface. One or more interface regions of the system user interface may be designated as limited remote access interface regions. The limited remote access interface regions present in screen data sent to a remote operator workstation for display may be modified such that, when displayed, they visually differ from respective unmodified interface regions. The modified interface regions may be displayed at the remote operator workstation for viewing by a remote operator. Systems and computer programs that afford functionality of the type defined by this method are also provided by the present technique.

Embodiments of the present technique relate to a medical diagnostic system/method employing a medical diagnostic-system application configured to generate a user-interface screen comprising a plurality of interface items of the medical diagnostic system. A configuration file stored on the medical diagnostic system contains identification data of the interface items, as well as a guarded designation for at least one guarded item. A dynamic link library is configured to receive the identification data and the guarded designation from the configuration file. A server is operative on the system for serving the user-interface screen of the medical diagnostic system to a remote client. Based on the identification data and guarded designation data received, the guarded item of the user-interface screen served to the remote client may have an altered appearance to the remote client and/or may be inoperable to the remote client.

DRAWINGS

The foregoing and other advantages and features of the invention will become apparent upon reading the following detailed description and upon reference to the drawings in which.

DETAILED DESCRIPTION

Figure 1:
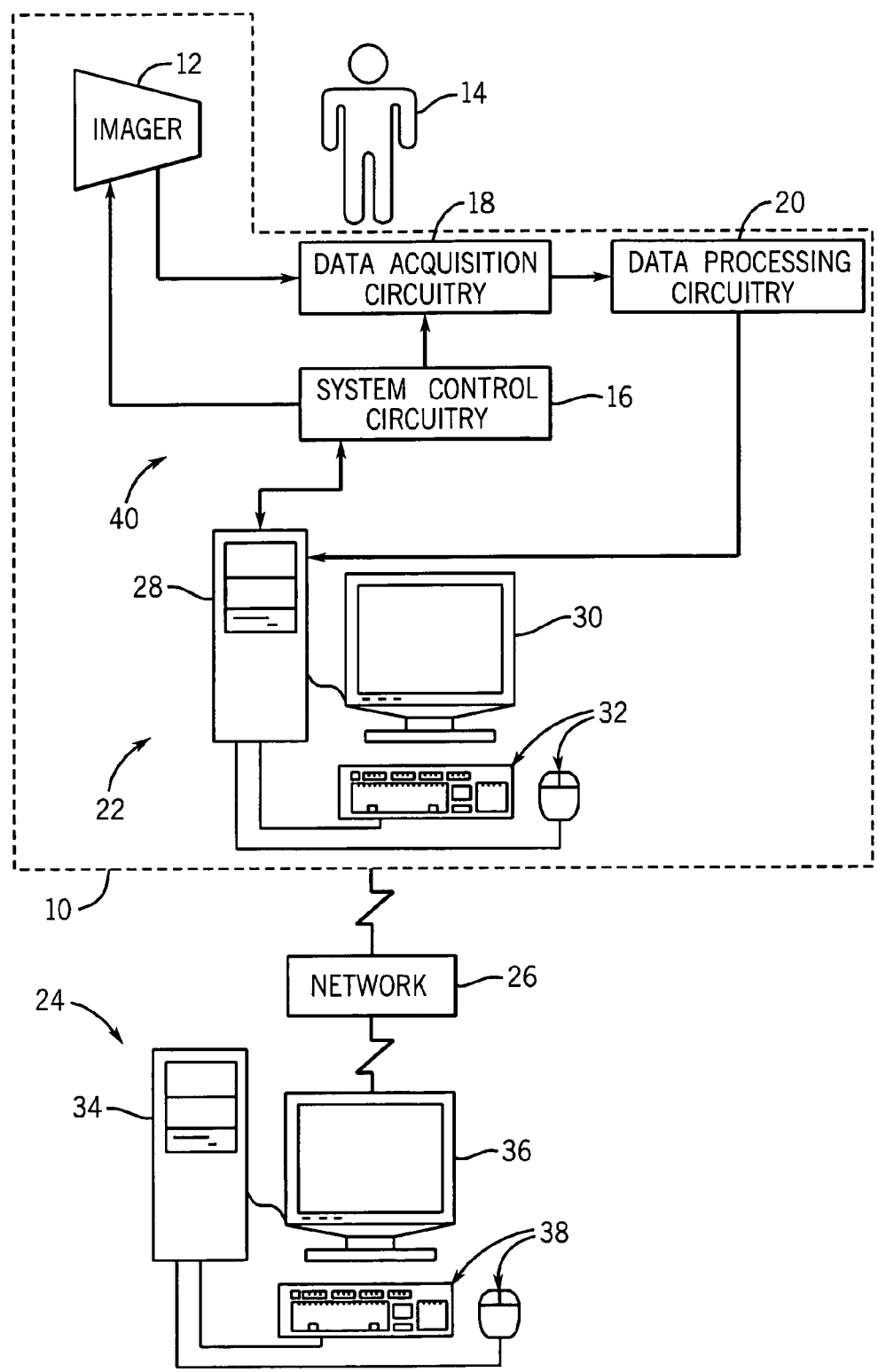
FIG. 1 is a diagrammatical representation of certain functional components of an exemplary generic imaging system configured for remote operation in accordance with embodiments of the present technique.

Turning now to the drawings, and referring first to FIG. 1, an exemplary medical imaging system 10 is depicted. Such systems are typically complex and require periodic maintenance of the system 10 and/or periodic instruction of the technicians or personnel using the system 10. The availability of qualified service engineers and/or instructors may be limited, however. The limited numbers of qualified personnel and the prevalence of the imaging systems 10 may, therefore, make remote service or instruction desirable where possible. However, it may also be desirable to limit the possible actions such a remote operator is allowed to perform, such as to prevent remote actions leading to the motion of moving components, the emission of X-rays, and/or the generation of strong magnetic fields. These various factors, alone or in combination, contribute to the challenges posed by remote operation of many types of medical imaging systems 10. Such challenges are addressed in the present technique. In accordance with aspects of the technique, a remote operator, such as a service engineer and/or instructor, may be provided with a limited visual interface and/or a limited input interface. In this manner, the remote operator is only presented with information or options corresponding to the desired scope of the remote task.

For example, returning to FIG. 1, an exemplary medical imaging system 10 is depicted. Generally the imaging system 10 includes some type of imager 12 that detects signals and converts the signals to useful data. As described more fully below, the imager 12 may operate in accordance with various physical principles for creating the image data. In general, however, the imager 12 creates image data indicative of regions of interest in a patient 14 either in a conventional support, such as photographic film, or in a digital medium.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements for storing programs and routines executed by the system control circuitry 16 or by associated components of the system 10.

The imager 12, following acquisition of the image data or signals, may process the signals, such as for conversion to digital values, and forward the image data to data acquisition circuitry 18. In the case of analog media, such as photographic film, the data acquisition system may generally include supports for the film, as well as equipment for developing the film and producing hard copies that may be subsequently digitized. For digital systems, the data acquisition circuitry 18 may perform a wide range of initial processing functions, such as adjustment of digital dynamic ranges, smoothing or sharpening of data, as well as compiling of data streams and files, where desired. The data may then be transferred to data processing circuitry 20 where additional processing and analysis are performed. For conventional media such as photographic film, the data processing system may apply textual information to films, as well as attach certain notes or patient-identifying information. For the various digital imaging systems available, the data processing circuitry 20 perform substantial analyses of data, ordering of data, sharpening, smoothing, feature recognition, and so forth. The acquired images or image data may be stored in short or long-term storage devices, such as picture archiving communication systems, which may be comprised within or remote from the imaging system 10.

The above-described operations and functions of the imaging system 10 may be controlled by a local operator workstation 22, which typically interfaces with the system control circuitry 16. The local operator workstation 22 may include one or more general purpose or application specific computers 28 or processor-based components. The local operator workstation 22 may include a monitor 30 or other visual display and one or more input devices 32. The monitor 30 and input devices 32 may be used for viewing and inputting configuration information or for operating the imaging system 10, in accordance with the techniques discussed herein. As with the system control circuitry 16, the local operator interface station 22 may comprise or communicate with a memory or data storage component for storing programs and routines executed by the local interface station 22 or by associated components of the system 10. It should be understood that any type of computer accessible memory or storage device capable of storing the desired amount of data and/or code may be accessed by the local operator workstation 22. Moreover, the memory or storage device may comprise one or more memory devices, such as magnetic or optical devices, of similar or different types, which may be local and/or remote to the system 10.

It should be noted that more than a single local operator workstation 22 may be provided. For example, an imaging scanner or station may include an interface which permits regulation of the parameters involved in the image data acquisition procedure, whereas a different operator interface may be provided for manipulating, enhancing, and viewing resulting reconstructed images.

In addition, a remote operator workstation 24 may communicate with the imaging system 10, such as via a network 26. The network 26 may be a local intranet within the medical facility, a service network between the facility and a service provider, a direct communication line between the imaging system 10 and the remote workstation 24, a virtual private network established over the Internet, the Internet itself, and so forth. In general, the network 26 allows data exchange between the remote workstation 24 and one or more components of the imaging station 10. As will be appreciated by those skilled in the art, any suitable circuitry, such as modems, servers, firewalls, VPN's and so forth may be included within the network 26.

The remote operator workstation 24 includes many, if not all, of the similar components of the local operator workstation 22, such as a processor-based computer 34, monitor 36, and input devices 38. On the other hand, the remote operator workstation may be a mobile computer or laptop, for example. The workstation 24 may also be a computer or workstation located at a remote servicing center, for example. The remote operator workstation 24 allows a remote operator to access elements of the imaging station 10 via the network 26. In particular, the remote operator workstation 24 may allow a remote operator to configure parameters associated with a scanning operation, to access or initiate service operations, to configure the processing of acquired scan data, and so forth.

However, it may be desirable to limit the access allowed a remote operator. In particular, because a remote operator cannot visually monitor the physical location of the imaging system 10, it may be desirable to prevent the remote operator from taking actions affecting the site. For example, absent some mechanism for visual monitoring, it may be desirable to prevent a remote operator from moving components of the imaging system 10, such as tables, gantries, mechanical arms, and so forth, and from generating radiation or magnetic fields at the site. Similarly, it may be desirable to limit the patient data provided to a remote operator to data relevant to the remote operation. For example, a service engineer or instructor who is assisting in a patient scan may need to know certain medically relevant facts to facilitate the procedure. However, other information, such as patient name, unrelated medical history, demographic information, billing information, insurance, and so forth, may be irrelevant to the functions performed by the remote operator.

It may therefore be desirable to include a guarding system to monitor and/or modify communication between the remote operator workstation 24 and the imaging station 10. The guarding system may include one or more routines executed by a portion of the network 26 or by the imaging system 10. For example, the guarding system may include one or more routines run on a server or component of the network 26 which is in the communications path between the remote interface station 24 and the imaging station 10. Similarly, the guarding system may include one or more routines run on one or more components of the imaging station 10 which are in the communication path to the remote interface station 24, such as the local interface station 22 or the system control circuitry 16. Indeed, the routines comprising the guarding system 50 may even be stored and executed on the remote interface station 24 if desired. For example, the guarding system may be implemented on a service server within the communication path of the network 26. The service server may be a within the service network provided by the service or instruction provider, such as at a remote service facility, or may be within the local network or intranet of the medical facility.

The guarding system may allow different limitations or security to be placed on the remotely accessible data. For example, one or more routines comprising the guarding system may be implemented on the service server or other platform at the medical facility that processes communication with the remote operator workstation 24. The guarding system may communicate with applications on the imaging station 10 and/or the remote operator workstation 24 via one or more specific communication interfaces, such as a Unix named pipe interface. The guarding system may act on the named pipe interface or other communication interface to affect control over what data is sent to and/or what data is received from the remote operator workstation 24.

For example, the guarding system may allow portions of the user display screen to be specified for monitoring or for modification when displayed remotely. Based on the graphical user interface (GUI) utilized by the software and control programs of the imaging system 10, portions of the display screen may be designated for modification, masking, monitoring, and so forth based on the selected communication pipe, i.e., local or remote connections. In particular, portions of the display screen corresponding to user interface elements, such as buttons, menu selections, sliders, and so forth, or data screens, such as patient name, may be so designated. For example, a limited command interface, typically local to the imaging system 10, may be present which allows an operator to designate user interface elements for special handling by the guarding system. In this way, restricted user interface elements of the imaging system 10 may be designated at the limited command interface, allowing differential processing of the local and remote user interfaces by the guarding system. The designation of the user interface elements at the limited command interface may be by identification of particular pixels or Cartesian coordinates corresponding to a portion of the screen to be regulated. Alternatively, the restricted status may be a property of standardized objects, depending on the GUI employed, which may be set to restrict remote access.

The unique location or identifying designation of restricted objects, pixels, or screen locations may be referred to as interface regions and may be established at the guarding system for differential handling of remote viewing and operations. In addition, where cascading screens may be employed or where parent screens may give rise to child screens, depending on the GUI employed, provision may be made in the guarding system for dynamically adjusting to accommodate for windows which are moved or rescaled. Similarly, functions or options in a child screen which are related to a restricted interface region in the parent screen may be configured to inherit the restrictions of the parent. In this manner, the protections provided by the guarding system may not be obviated or circumvented by moving or resizing a window of the GUI or by accessing a restricted function or data via a child window.

Examples of the types of differential handling that may be implemented by the guarding system include blocking and guarding functions. For example, blocking an interface region would prevent the display of the interface region on the remote operator workstation 24 and would prevent user action in the interface region, i.e., selecting or clicking on a masked button. Similarly, guarding an interface region would prevent user action in the interface region, however the contents of the guarded interface region may be visible to the remote operator. However, to allow a remote operator to know that an interface region is guarded, the guarded interface region may be visually differentiated, such as by differential coloring, tinting, brightness, patterning, hatching, shading, and so forth.

In a particular example, a service interface to a medical diagnostic system or device allows operation of the diagnostic system (e.g., scanner) from a remote location, using a set of user interface controls that are similar or duplicative (or a partial duplicate) of the local operator console controls. In one embodiment, this feature of providing a remote duplicate interface is labeled "Remote Console Observation and Control" or RCOC. Using the RCOC, a workstation desktop of the medical diagnostic system (e.g., medical scanner) can be viewed on a remote machine, thus providing for sharing of the desktop for various purposes, such as for training of applications, and so on.

In order to provide for the safe and appropriate operation of the medical diagnostic system or modality, guard features may be implemented in the guarding system (e.g., RCOC) whereby parts or portions of the desktop are guarded at the remote location so that the remote user cannot operate the commands underlying those guarded portions of the desktop. This guard or lockout feature may prohibit, for example, the remote user from deleting patient information stored within the diagnostic system or from moving certain hardware parts via the software buttons on the desktop, etc. It should be noted that while the remote operator cannot employ the guarded commands these guarding or lockout features can be applied in such a way as not to significantly disturb the clinical efficacy of the medical diagnostic device when operated remotely.

These guarding or lockout features may be implemented in both Unix (e.g., Unix/X) and/or Windows, for example. The features can be configured using the window/command identification numbers or through the window/command signatures. Such approaches may in Windows platforms generally obtain a software application's handle or its child command's handle as a runtime activity. Commonly, window/command handles are allotted at runtime and are typically unique within the application of the diagnostic system or modality application.

In this context in the Windows platform, there are a variety of options to guard or block the windows/commands on a remote interface using a guarding system (e.g., RCOC). One option is to link to a guarding library at compile time and runtime, call the guard application program interfaces (API's) inside the diagnostic-system application, and then run the application. Unfortunately, the medical diagnostic system/modality application is configured or revised to call the guarding API's within its code. A concern with this approach is that the diagnostic-system application may be more prone to fail with guard API's links written into their code. In other words, the writing of code into the modality application to link to the guarding API library could cause failure of the modality application if there is a failure in the guard API library, for example.

Another option of guarding windows/commands in the Windows platform is to have a separate application running in the background that places guards on the windows/commands based on position or geometry by sending a diagram packet to the medical facility server coupled to the modality application. In this option, the guards may be implemented using a geometric system (x, y coordinates, width, height of the widget). A concern with this approach is the overhead associated with running a process in the background, errors in determining the external application window/commands geometry, and so forth.

Further improvements provide for writing a configuration file having the window class name and the window title names. To apply a guard to particular window or command of the remote desktop, the modality application places the class name and title name of the window/command in a Windows configuration file. A guard system or process (e.g., RCOC) reads the configuration file and applies the guard on the windows/commands of the remote screen view. Such guards can be applied automatically.

In certain embodiments, API's of the Windows software development kit (SDK) can be utilized. As appreciated by those skilled in the art, the SDK is generally a set of Windows operating system libraries. Examples of such API's provided by the SDK in the Windows platform and employable by embodiments of the present technique are EnumWindows( ), EnumChildWindows( ), and so on. These API's generally iterate through the windows and the child windows of the modality application on a given desktop, facilitating application of guards on the windows/commands (e.g., via the RCOC). Advantageously, the medical diagnostic-system application may avoid incorporating guarding code directly. Instead, guarding is achieved by placing the class name and/or title name of the window/command into the external configuration file. As a result, the guarding feature does not disturb the clinical applications(s) because the code is separated by a robust Windows interface.

Figure 2:
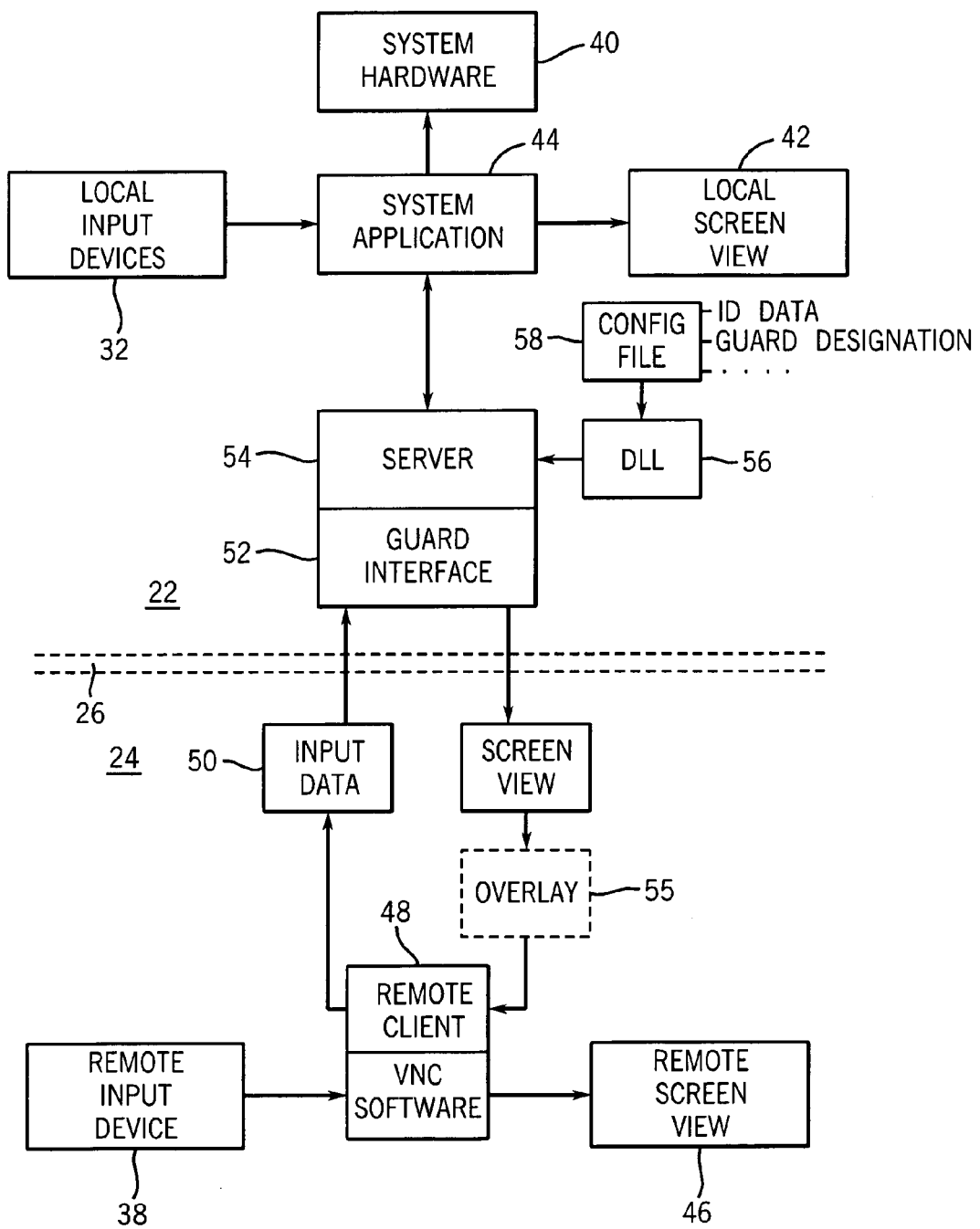
FIG. 2 is diagrammatical representation of local and remote workstations, the remote workstation having limited access via a guard interface in accordance with embodiments of the present technique.

FIG. 2 depicts the local operator workstation 22 and the remote operator workstation couple by the network 26. As indicated, both workstations 22 and 24 include inputs devices 32 and 38 (e.g., mouse, keyboard, etc.). The medical-diagnostic system hardware 40 and a local screen view 42 for the modality system application 44 are depicted at the local operator workstation 22.

The remote screen view 46 is observed by the remote client 48 or user who may input commands via remote input device(s) 38 and virtual network computer (VNC) software. The VNC may employ a remote frame buffer protocol and format the input data 50, for example. Such sharing systems, which may be platform independent, may transmit the keyboard presses and mouse clicks as input data 50 (e.g., TCP/IP packets) over the network 26 and through a guard interface 52 to the server 54, and ultimately to the system application 44. Such sharing systems may be platform independent. Generally, multiple remote clients 48 may connect to a VNC server.

The guard interface 52 may filter the input data 50 to remove or eliminate remote inputs which originated from a selection by the remote client 48 within a guarded or blocked interface region. The resulting filtered inputs flow to the system application 44 of the medical diagnostic system via the server 54, for example. The present technique allows a remote operator, such as an engineer or technician, to remotely access the system application 44 in a controlled manner while preserving patient confidentiality and any desired local control over the physical site. The guard interface 52 and server 54 may incorporate a C++ server, for example, running at or external to the medical diagnostic system. Indeed, in certain embodiments, the server 54 is a C++ server.

Screen updates may transmit from the system application 44 to the remote screen view 46 in the reverse path. The guard interface 52 may place an overlay 55 (e.g., transparent overlay) on the remote screen view 46. The overlay may color the guarded items or buttons on the remote screen view 46, for example, to guard and indicate the blocked access of those items to the remote client 48. The remote screen view 46, complete with guards and blocks, may be displayed on the remote operator workstation 24 for viewing or manipulation by the remote operator. The remote operator may interact with unguarded and unblocked interface regions of the remote screen view 46 to generate remote user inputs 50 directed to system application 44 of the medical diagnostic system (e.g., imaging system).

In certain implementations, a dynamic link library (DLL) 56 coupled to the guard interface via the server 54 and receives input from a configuration file 58 having the identification data, guard designation data, and so on, of the system application 44. The configuration file 58 may contain the identification or locations of items or buttons to be colored, guarded, blocked, and so forth, of the remote screen view 46 at the remote client 48. For example, the configuration file 58 may designate the buttons or items to be guarded by coordinates (i.e., of the window or desktop), identification number or data, name of the item, and so on. In operation, the DLL 56 receives input (e.g., window identification, location, and measurement) from the configuration file 58. The DLL 56 may contain locations of items and will generally provide information (identification number, name, coordinates, dimensions, and/or guard labels, etc.) to the guard interface 52 and server 54.

The configuration file 58 may be created external to the system application 44 and may generally be reprogrammed, as needed. In some examples, the system application is restarted to implement the changes to the configuration file. The guard interface 52 creates the transparent overlay 55 with a colored guard (e.g., in green or red). In certain cases, the color guard may only appear as the cursor passes over the guarded item. On the other hand, the items or buttons may remain colored or depicted as guarded in some manner, whether or not the cursor is on the button or item. Moreover, the guard interface 52 may involve both a static guard process (i.e., in the configuration file 58) and a dynamic guard process which can be implemented on the fly, e.g., by right-clicking on the guard or by other means.

In sum, in these embodiments, the guard interface 52 combine with a server 54 (e.g., C++ server) at the system application 44. The server 54 may be generated separate from the application software of the system application 44. The guard interface 52 having the server 54 may provide for coordinates, identification number, name of the region to be guarded, and the like, to guard buttons or items. Such information may be received from a configuration file 58 prepared separately from the system application 44. The configuration file 58 may identify what buttons or items and/or what coordinates of the desktop to guard (e.g., to color or alter the appearance in other manners, and to block access to the remote client 48). The server 54 or guard interface 52 links to a DLL 56 which may be written separately from the system application 44, such as by the manufacturer or a service group of the medical diagnostic system. It should be readily apparent that it may be advantageous for a service group to be able to prepare the configuration file 58 substantially independent of the application 44. Lastly, based on input from the configuration file 58, the server 54 or guard interface 52 creates an overlay to guard items or buttons (e.g., shown as colored when the cursor is dragged over the guarded item or button). Therefore, this example employs more than straight UNIX, relying on the Windows configuration file 58 to guard windows.

Figure 3:
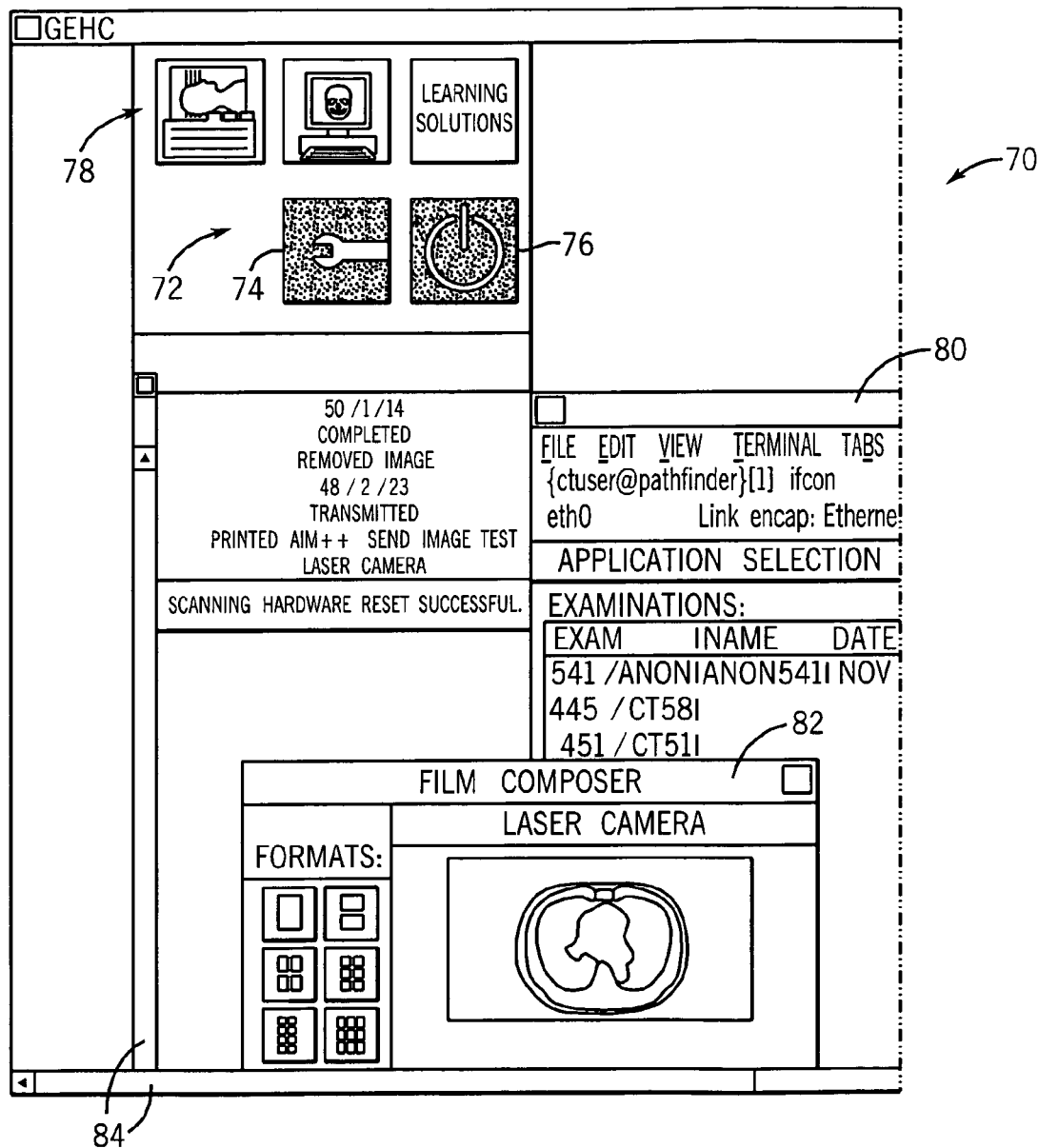
FIG. 3 is a diagrammatical representation of an exemplary remote screen in accordance with embodiments of the present technique.

FIG. 3 depicts an exemplary representative screenshot of a remote (view) display 70 of an application desktop of a medical imaging system or scanner in accordance with the present technique. The remote display 70 has a guard overlay. In this embodiment, the display provides five buttons 72 operable to the local user who is positioned locally at the medical diagnostic system. However, the service button 74 and the power button 76 are inoperable to the remote user, as indicated by the discoloration. These two buttons have a colored (e.g., green) transparent guard. Therefore, only the three buttons 78 along the top row are operable to the remote user.

In this example, the service button 74 may be depressed to initiate service of the medical diagnostic system (e.g., scanner). The power button 76 is an on/off button used to shutdown and power up the system. These two buttons 74 and 76 are not operational at the remote computer because, in this particular case, the remote user does not know or cannot recognize whether a patient is situated in the scanner. Therefore, the remote user is not permitted these two shielded buttons 74 and 76 with his mouse or keyboard. Accordingly, in this example, the remote user will not be able to turn off the scanner or to service it remotely because of the static or dynamic guarding applied by the guarding system (e.g., RCOC).

The remote display 70 may have multiple additional windows 80 and 82 active and in view. Such windows may contain a variety of information related to the scanner, patient, images, data, current session, and so forth. Further, the desktop may contain typical scroll bars 84 for manipulating the views of the various windows.

Figure 4:
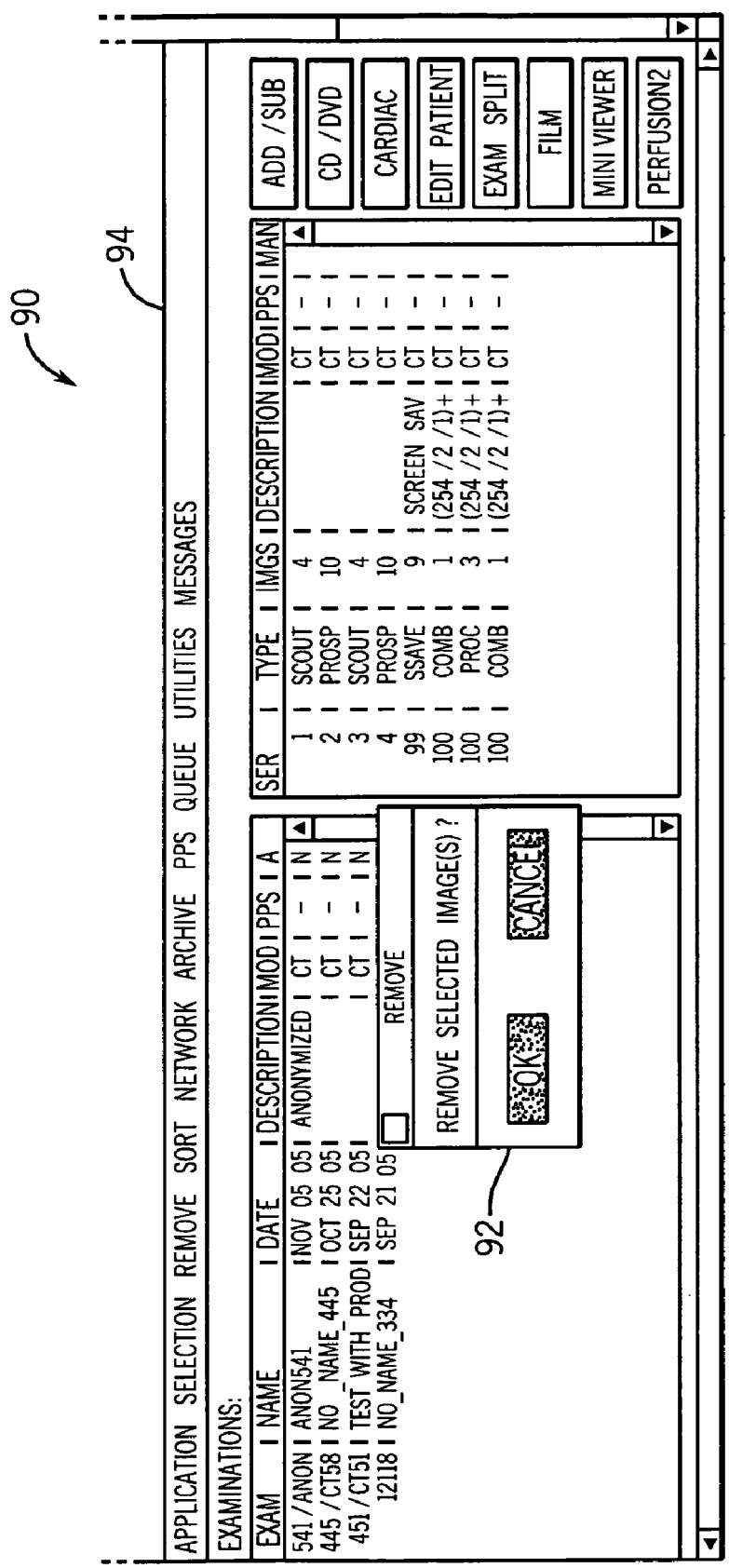
FIG. 4 is a diagrammatical representation of an exemplary remote screen in accordance with embodiments of the present technique.

FIG. 4 depicts a representative screenshot of a remote display 90 of a medical diagnostic system. The remote display 90 presents a pop-up window 92 that is guarded from the remote user in accordance with the present technique. In this embodiment, the pop-up window 92 (Remove Image) appears on top of a main window 94 and is guarded by a dynamic guard. As a result, the remote user cannot delete a patient specific data (e.g., images, prescriptions, etc.). In particular, the remote user in this example cannot click the confirm button to confirm the pop-up window 92 with the mouse/cursor because the confirm button on the pop-up window 92 is inoperable (and colored) to the remote user.

Figure 5:
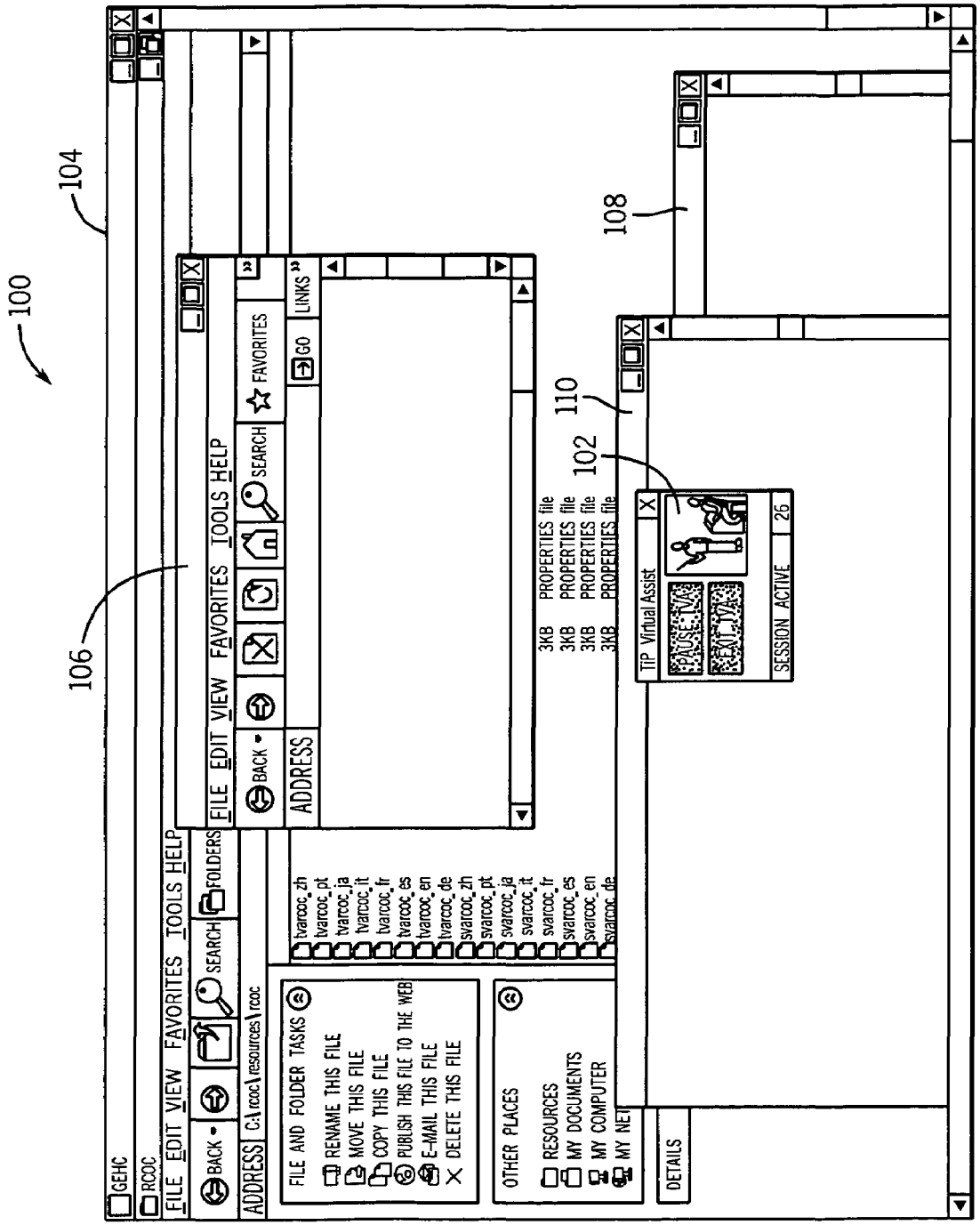
FIG. 5 is a diagrammatical representation of an exemplary remote screen in accordance with embodiments of the present technique.

FIG. 5 depicts a representative screenshot of a remote display 100 of a user interface of a medical diagnostic system for a training mode. In this example, the window 102 (e.g., of the RCOC) has a teacher icon. The two buttons (pause and exit) on the window 102 are colored and inoperable to the remote user in accordance with the present technique. The remote user in the case cannot pause or cancel the training session by clicking on the RCOC user interface button "pause TVA" or "Exit TVA," respectfully. It should be noted that portions of the desktop 104 or other windows 106, 108, and 110 can also be guarded, either statically or dynamically. Further, such guards may or may not be related to operation or training with regard to the medical diagnostic system.

Though the present technique has been discussed in regard to general imaging technologies, one of ordinary skill in the art will readily appreciate how it may be adapted to specific imaging modalities. For example, the present technique may be applied to computed tomography (CT) systems to allow remote configuration and access to the imaging system while preventing remote movement of the gantry or patient table and remote activation of the X-ray source. Another example of an imaging system 10 is a magnetic resonance imaging (MRI) system. The MR system controller will generally permit some amount of adaptation or configuration of the examination sequence by means of a local operator interface 22 or remote operator interface 24, in accordance with the technique described herein.

As in the case of the foregoing imaging systems, MR image data may be viewed locally at a scanner location, or may be transmitted to remote locations, such as the remote operator interface 24, both within an institution and remote from an institution such as via network 26. In addition, configuration and operation commands and instructions may be provided to MR system controller via the local or remote operator interfaces 22, 24. As discussed herein, a portion of the data transmitted to and instruction received from the remote interface 24 may be blocked or guarded via the guard interface 52 operating between the remote interface 24 and the respective components of the MR system.

In addition to MR and CT systems, other medical imaging modalities may benefit from the present technique, as will be appreciated by one of ordinary skill in the art. For example, tomosynthesis, electron beam tomography (EBT), positron emission tomography (PET), and nuclear medicine systems may benefit from limited remote operator access for service or instruction. The movement of system components or the operation of the respective radiation sources, however, may be guarded or blocked in accordance with the present technique to limit remotely initiated actions.

The technique disclosed herein, however, is not limited to the specific applications described, but may be applied in other contexts as well. For instance, the technique may be employed with imaging devices outside the medical field, such as in part inspection, baggage inspection, and quality control. Indeed, the technique may be employed with any device that may benefit from the implementation of limited or regulated remote access, such as for training or service, in which certain functionalities of the device are to remain under local control.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of guarding an item in a remote display of an interface of a medical diagnostic system comprising:
   writing a configuration file comprising identification information of displayed items of the interface in the remote display;
   storing a guard designation in the configuration file for at least one guarded item of the interface in the remote display;
   creating a dynamic link library configured to receive the identification information and the guard designation from the configuration file; and
   installing a server to receive input from the dynamic link library, wherein the server is configured to call an application program interface (API) function that outputs identification information of displayed items of the interface in the remote display, to compare the identification information output from the API function to the identification information from the configuration file, and to guard at least one displayed item based on the comparison.

2. The method as recited in claim 1, wherein the server is configured to serve the remote display so that the guarded item comprises an altered appearance on the remote display.

3. The method as recited in claim 1, wherein the server is configured to serve the remote display so that the guarded item is inoperable via the remote display.

4. The method as recited in claim 1, wherein the guarded item is configured to control a physical operation of the medical diagnostic system.

5. The method as recited in claim 1, wherein the medical diagnostic system comprises a medical imaging system.

6. A method of operating a medical diagnostic system, comprising:
   comparing identification information output from an application program interface (API) function of an operating system software development kit (SDK) to identification information of an item to be guarded on a remote display from a configuration file;
   receiving information from the configuration file to a dynamic link library;
   receiving input from the dynamic link library to a server coupled to the medical diagnostic system; and
   guarding the item to be guarded on the remote display based on the identification information and the comparison.

7. The method as recited in claim 6, comprising serving the remote display via the server.

8. The method as claim 7, comprising altering the appearance of the guarded item on the remote display via the server based on the input received from the dynamic link library.

9. The method as recited in claim 7, comprising guarding access to the guarded item on the remote display by a filter implemented by the server based on the input received from the dynamic link library.

10. The method as recited claim 9, wherein the guarded item is configured to control a physical operation of the medical diagnostic system.

11. The method as recited in claim 6, wherein the server comprises a C++ server.

12. A medical diagnostic system comprising:
   an application configured to generate a user-interface screen comprising a plurality of interface items and to call an application program interface (API) function of an operating system to identify displayed interface items;
   a configuration file stored on the system and including identification data of at least one interface item to be guarded and a guarded designation for the at least one guarded item;
   a dynamic link library configured to receive the identification data and the guarded designation from the configuration file; and
   a server operative on the system for serving the user-interface screen to a remote client.

13. The method as recited in claim 12, wherein the guarded item of the user-interface screen served to the remote client has an altered appearance to the remote client.

14. The method as recited in claim 13, wherein the medical diagnostic system comprises a scanner.

15. The method as recited in claim 12, wherein the altered appearance is based upon the identification data and the guarded designation.

16. A medical diagnostic system comprising:
   an application configured to generate a user-interface screen comprising a plurality of interface items and to call an application program interface (API) function of an operating system to identify displayed interface items;
   a configuration file stored on the system and including identification data of at least one interface item to be guarded and a guarded designation for the at least one guarded item;
   a dynamic link library configured to receive the identification data and the guarded designation from the configuration file; and
   a server configured to serve the screen to a remote client and to receive inputs from the remote client based upon the screen.

17. The system as recited in claim 16, wherein the server is configured to disallow functions of the application corresponding to the guarded item.

18. The system as recited in claim 16, wherein the at least one guarded item is configured to control a physical operation of the medical diagnostic system.

19. The system as recited in claim 16, wherein the medical diagnostic system comprises a medical imaging system.

20. The system as recited in claim 19, wherein the medical imaging system comprises one of a CT imaging system, an MRI imaging system, a tomosynthesis system, an EBT imaging system, a PET imaging system, or a digital X-ray imaging system.

* * * * *